United States Patent [19]

Herdle et al.

[11] 4,255,348

[45] Mar. 10, 1981

[54] PREPARATION OF DIMETHYLAMINOSILANES

[75] Inventors: William B. Herdle, Greenburgh; Bernard Kanner, West Nyack, both of N.Y.

[73] Assignee: Union Carbide Corporation, New York, N.Y.

[21] Appl. No.: 87,797

[22] Filed: Oct. 24, 1979

[51] Int. Cl.$^3$ .............................................. C07F 7/08
[52] U.S. Cl. .................................................... 556/410
[58] Field of Search ................................. 260/448.2 T

[56] References Cited

U.S. PATENT DOCUMENTS

| | | | |
|---|---|---|---|
| 2,380,996 | 8/1945 | Rochow et al. | 260/607 |
| 2,483,373 | 9/1949 | Rochow | 260/448.2 |
| 2,887,501 | 5/1959 | Bluestein | 260/448.2 |
| 3,467,686 | 9/1969 | Creamer | 260/448.2 |
| 3,951,710 | 4/1976 | Boni | 156/17 |
| 4,088,669 | 5/1978 | Malek et al. | 260/448.8 R |

OTHER PUBLICATIONS

Fessenden et al., "Chem. Rev.", pp. 361–388, 1961.
Newton et al., "Inorg. Chem.", 9, pp. 1071–1075 (1970).
"J. Chem. Soc.", pp. 3429–3436 (1964).
Declerq et al., "J. Electrochem. Soc.", 122, pp. 545–552 (1975).
"Chem. Abs.", 52, 2692b (1958).
"Chem. Abs.", 76, 28552z (1972).
"J.A.C.S.", 67, pp. 963–965 (1945).
Voorhoeve, "Organohalosilanes: Precursors to Silicones", Elsevier, Amsterdam (1967), pp. 122–137, 160, and 161.
Kirk-Othmer, "Encyclopedia of Chemical Technology", 2nd Ed., 6, pp. 139, 141, & 170, John Willey & Sons (1965).
Bazant et al., "Organosilicon Compounds", vol. 1, Academic Press, N.Y. (1965), pp. 77–85.

*Primary Examiner*—Paul F. Shaver
*Attorney, Agent, or Firm*—Richard J. Gallagher

[57] ABSTRACT

Process for preparing dimethylaminosilanes by reacting silicon with dimethylamine.

10 Claims, No Drawings

PREPARATION OF DIMETHYLAMINOSILANES

BACKGROUND OF THE INVENTION

This invention relates to a novel process for preparing dimethylaminosilanes. More particularly, this invention relates to a novel process for preparing dimethylaminosilanes by reacting particulate silicon with dimethylamine.

Dimethylaminosilane compounds are well known in the art as are various methods for their preparation. For instance the most common method for preparing such silanes is by the reaction of dimethylamine and a halosilane. Other methods that have been reported involve the reaction of an amine with silicon sulfide ($SiS_2$) or an organometallic silane, the reaction of a hydridosilane with an amide and reactions involving the exchange of one amino group for another on silicon. All such methods have at least one common disadvantage in that they all require that the silicon be first converted to an intermediate material (e.g. chlorosilane) prior to formation of the desired aminosilane. Moreover, such an extra step in the formation of dimethylaminosilanes can also lead to undesirable by-products that must also be removed from the desired aminosilane product. This latter drawback is especially evident in the reaction of chlorosilane with dimethylamine which liberates undesirable hydrogen chloride.

It has now been surprisingly discovered that dimethylaminosilanes can be easily obtained by employing the process of this invention which comprises directly reacting particulate silicon with dimethylamine.

SUMMARY OF THE INVENTION

Thus it is an object of this invention to provide a novel process for producing dimethylaminosilanes. Other objects and advantages of this invention will become readily apparent from the following description and claims.

More specifically this invention can be described as a process for preparing a dimethylaminosilane having the formula $$H_{4-a}Si[N(CH_3)_2]_a$$

wherein a has a value of 2 to 4 inclusive, said process comprising reacting (1) copper activated silicon particles and (2) dimethylamine gas in a gas-solid reactor at a temperature in the range of about 195° C. to about 400° C.

DESCRIPTION OF THE PREFERRED EMBODIMENTS

Thus this invention as pointed out above merely involves contacting copper activated silicon in particulate form with dimethylamine gas in a gas-solid reactor by passing said dimethylamine over the copper activated silicon particles at a temperature in the range of about 195° C. to about 400° C. to produce the desired dimethylaminosilane compounds which products are easily recovered by condensing the dimethylaminosilane effluent gases that exit the reactor.

The particular type and design of the gas-solid reactor system employed in this invention is not critical and any conventional reactor system such as a fixed bed reactor, a stirred bed reactor, a fluid bed reactor, or combinations thereof, which is suitable for gas-solid reactions should be applicable for this invention. Reactor systems which provide for suspending the solid in an inert liquid, however, are not desirable since they may fail to provide for adequate contact between the silicon and dimethylamine gas.

In general it is preferred to carry out the process of this invention while the silicon particles are in a state of agitation, such as that caused by a stirred (mechanically agitated) bed reactor or a fluid (gas agitated) bed reactor or a combination of such reactors in which the silicon particles can be agitated by both such methods if desired. More preferably the process of this invention can be carried out in any conventional fluid bed reactor whereby the dimethylamine gas is fed to the reactor at a rate sufficient to fluidize (suspend and agitate) the bed of silicon particles which are heated in the reactor zone at temperatures of about 195° C. to about 400° C., preferably about 230° C. to about 270° C. to thereby produce a gaseous effluent reaction mixture which is then condensed and from which the desired dimethylaminosilane products can be obtained. Of course, it is understood that the particular operational details of such reactor systems are also conventional and well known in the art and thus need not be fully detailed since such can readily be adapted to and employed in this invention.

For instance, as is common in fluid bed reaction systems the dimethylamine gas in the process of this invention is normally fed to the reactor at a rate at least sufficient to fluidize the bed of silicon particles, but below such a rate that would carry an undesirable amount of unreacted silicon particles beyond the heated reaction zone. The particular flow rate of dimethylamine gas employed for a given process is of course, merely dependent upon such obvious factors as the particular apparatus employed, the amount of silicon employed, etc. and may be easily determined and controlled by conventional procedures. Of course, it is to be understood that if desired the fluidization of the silicon particles may also be aided by the use of an inert gas such as nitrogen, and the like, however, the use of such an inert gas is not necessary nor generally recommended.

The dimethylamine gas then reacts with the copper activated silicon particles while fluidizing same in the heated reaction zone of the reactor to form effluent gases of dimethylaminosilanes, hydrogen and other minor by-products which exit the heated reaction zone to a condensing chamber wherein the desired dimethylaminosilane products can be condensed into liquid form and recovered from a product reservoir in any conventional manner desired. An imporatant by-product of the reaction is hydrogen gas which can be recovered or disposed of if desired by withdrawing same from the condensing chamber while any inert gas, such as nitrogen, when employed, can also be removed at this point. Likewise, any unconsumed solid particulate material that may remain after the reaction can be recovered and disposed of if desired by any suitable conventional method. Any unreacted dimethylamine which has been initially condensed with the product effluent can, of course, be withdrawn as a gas directly from the product reservoir or distilled from the recovered product effluent and may be purified and reused, if desired. The condensed liquid effluent can be recovered from the product reservoir in any suitable manner and filtered to remove any elutriated fine particles of unreacted silicon, if necessary. Alternatively, a cyclone separator or other device for separating entrained solids may be inserted at the reactor exit to collect elutriated particles. The desired dimethylaminosilane products can then be easily recovered and isolated by any conventional method, such as distillation. The major product is generally tris-dimethylaminosilane (boiling point 142° C.) having the formula $HSi[N(CH_3)_2]_3$ which can amount to 90 percent or more of the total condensed reaction product after removal of unreacted dimethylamine. Bis-dimethylaminosilane (boiling point 93° C.) having the formula $H_2Si[N(CH_3)_2]_2$ generally represents from 3 to 8 percent, more usually about 4 percent, of the product, while tetrakis-dimethylaminosilane (boiling point 196° C.) having the formula $Si[N(CH_3)_2]_4$ usually represents about 1 percent of the product. However, under some conditions as seen by the examples herein below tetrakis-dimethylaminosilane may be formed as the principal product. Other minor dimethylaminosilicon reaction products normally representing together less than 5 percent of the condensed reactor effluent product include disilanes, disilazanes, oligomers, and the like.

As pointed out above, the silicon particles employed in this invention must be activated with copper for the reaction to be successful since pure silicon is not reactive toward dimethylamine in the absence of copper, which acts as a catalyst for the reaction. Thus the term, "copper activated silicon", as employed herein, means any mixture or alloy of copper and silicon that will react with dimethylamine gas at a temperature in the range of about 195° C. to about 400° C. as described herein. In general, two requirements must be fulfilled by a copper silicon mixture or alloy in order that it be reactive in this invention. The first requirement is that the silicon and copper must be in intimate contact. This may be accomplished, for example, by melting the silicon with the copper, permitting the melt to solidify, and grinding the resulting solid into particles, or alternatively by heating and/or grinding a mixture of silicon and copper particles, as disclosed e.g. by U.S. Pat. No. 2,380,996 and E. G. Rochow, "Journal American Chemical Society", Volume 67, page 963 (1945). It is believed that the copper becomes physically combined with the silicon particles during such treatment such as by diffusion. Yet another method of preparing a mixture of silicon and copper in suitable intimate contact is to treat silicon particles with copper salts, such as cupric sulfate or cuprous chloride, either by reaction with a solution of the copper salt or by heating. It is believed that copper formed in the resulting reducing process is physically combined with the silicon, such as deposition or diffusion. Other methods of preparing silicon-copper contact masses, such as those methods conventionally employed for the preparation of silicon-copper mixtures to be reacted with methyl chloride and well-known in the literature for this purpose, may be suitable for this invention. However, such contact masses must satisfy a second requirement beyond the intimate contact of silicon and copper, which is that they must have undergone during or after their preparation a process of activation. Such activation may be conducted by heating an intimate mixture such as those described above under an atmosphere of hydrogen at about 1000° C., or alternatively by treating such a mixture with hydrogen chloride or a compound that releases hydrogen chloride under the activation conditions at a temperature sufficient to permit reaction of the surface of the particles with the hydrogen chloride, e.g. at 300° C. It is believed that this invention step removes oxides from the surface of the silicon-copper particles, and other suitable methods for cleaning the particles and removing surface oxides may be employed for this purpose instead of those just described. For example, conventional methods of activating silicon-copper contact mixtures for reaction with methyl chloride as given e.g. by R. J. H. Voorhoeve, *Organohalosilanes: Precursors to Silicones*, Elsevier, Amsterdam, 1967, p. 129, may in some cases be useful for this purpose. Voorhoeve states that the presence of an oxide layer on the surface generally has a deleterious effect on reactions of silicon-copper with alkyl halides. It is believed that the reaction of silicon-copper with dimethylamine is even more sensitive to the presence of surface oxides and therefore requires additional attention to activation as described herein. Alternatively, the two steps described above may be combined into a single procedure whereby an intimate mixture of copper and silicon is simultaneously formed and activated. This may be accomplished, for example, by treating particles of silicon with solid cuprous chloride in a fluidized bed at about 230°–270° C. in an atmosphere of dimethylamine.

Moreover, it should be understood that elements other than silicon and copper may be present in the copper activated silicon, without detracting from the successful practice of our invention. Thus, although hyper-pure silicon may be useful for this invention, provided that it is treated with copper and suitably activated as described herein, commercially available silicon which may typically contain small amounts of other elements such as Al, Bi, Ca, Cr, Cu, Fe, Mn, Ni, Pb, Sn, and Ti, has been commonly employed herein; while mixtures of copper and copper oxides have been used as sources of copper in some preparations. However, the addition of large amounts of certain elements such as Pb is preferably to be avoided because they have an adverse effect on the rate of reaction. Furthermore, additives which have no demonstratable adverse effect on the practice of this invention can be employed, e.g. $ZnCO_3$, which is a well known promotor for the reaction of methyl chloride and silicon, has in some instances been employed during the preparation of the copper activated silicon.

More specifically copper activated silicon particles have been prepared and found useful in this invention in three different ways. One method involves contacting silicon particles and copper in a fluidized bed reactor by fluidizing the silicon particles with hydrogen chloride gas at about 300° C. and adding copper, preferably in the form of a finely divided mixture of copper and copper oxides (about 70–80% copper by weight), commonly known as cement copper, together with a small amount of a promotor such as zinc carbonate, and continuing the process until a vigorous reaction between silicon and hydrogen chloride is established. As a result of said process the copper becomes alloyed to and is widely distributed over the silicon surface. Activation and modification of the reactivity of copper-silicon alloys by hydrogen chloride treatment is well known in the art as seen, e.g., by U.S. Pat. Nos. 2,483,373 and 2,887,501. Alternatively, the copper activated silicon particles employable herein can be prepared by heating a mixture of elemental silicon particles and cement copper along with a small amount of a promotor, such as zinc carbonate, at about 1000° C. for about one hour under a slow stream of hydrogen gas. The in situ method of forming copper activated silicon particles employable herein merely involves adding finely divided anhydrous cuprous chloride to the silicon particles as they are being fluidized with dimethylamine preferably at about 250° C. The reaction of the silicon is dimethylamine begins almost instantly when the cuprous chloride is added. Other copper compounds may be employed in this method; it should be noted, however, that not every copper compound may be suitable since cement copper was not found to activate the silicon by this method.

Of course, it is to be understood that the amount ratio of copper to silicon employed to produce the activated copper-silicon particles employable in this invention is not narrowly critical and the amount of copper need only be that catalytic amount necessary to activate the silicon particles, i.e., render the silicon reactive with dimethylamine so as to permit the reaction to proceed at a desirable rate. In general, copper-silicon particles containing between about 0.5 and about 3 percent by weight of copper have been found to provide sufficient activation, although copper-silicon particles containing higher or lower amounts of copper may be employed if desired. Likewise, the particular type of copper compound employed for activation is not critical so long as it is one that will activate the silicon particles to react with dimethylamine. When preforming the copper activated particles it is preferred to employ a mixture of copper and copper oxides, such as cement copper, while cuprous chloride has been found to be suitable for the in situ method.

During long periods of storage in air or intimate contact with air the copper activated silicon particles can gradually lose their reactivity toward dimethylamine. This effect is believed to be due to the formation of a surface oxide layer. In addition to air and oxygen, water is also a suspected deactivation agent. For instance, injection of 50 mg of water or 50 cm$^3$ of air into the gas feed stream of a reactor in which 100 g of copper activated silicon particles was being reacted with dimethylamine immediately quenched the reaction (although activity reappeared after 0.5–1 hour of further treatment with dimethylamine). On the other hand, injection of 50 cm$^3$ of nitrogen under similar conditions caused no measurable loss of reactivity and copper activated silicon particles in sealed glass bottles under a nitrogen atmosphere have shown no apparent loss of activity over more than six months of storage. Contact of the copper activated silicon with air or water should therefore preferably be avoided, although storage in air for a few months may be possible without unacceptable loss of activity. However, we have found that reactivity may be restored in copper activated silicon particles that have lost their activity in this manner. This can be accomplished by subjecting the particles again to any of the activating methods described above, that is, by treating them with hydrogen chloride in a fluidized bed, by heating them under a hydrogen atmosphere, or by adding cuprous chloride or other suitable copper salt to the particles in a bed fluidized with dimethylamine at ca. 250° C.

The size distribution of the copper activated particles employable in this invention can take on any particle size commonly employed for solids in the conventional gas-solid type reactors mentioned above. In general it is preferred that the maximum silicon particle size be no more than about 30 mesh. Of course the most preferred particle size in any given reaction will merely depend upon the type of reactor employed, etc., and that size distribution which will help obtain the most optimum results desired can be easily determined by routine experimentation. For example, in laboratory experiments it was preferred to use 65 by 150 mesh fractions of said particles because this seemed to produce smoother fluidization in the laboratory reactor, but such size distribution is not necessary for reaction.

The process of this invention is indeed unique in that copper has been the only metal found to activate the silicon particles so that they can be reacted with dimethylamine. Likewise, dimethylamine has been found to be the only amine that can be sufficiently reacted with the copper activated silicon particles to successfully isolate aminosilane products from the exit stream of the reactor. The following amines have also been tried: ammonia, monomethylamine, diethylamine, pyrrolidine, t-butylamine and neopentylamine, however each of these amines was not found to produce isolatable aminosilane products with the copper activated silicon particles employable in this invention. Furthermore, the addition of any of these other amines to the feed stream of dimethylamine quenched that reaction. If the amount of added amine was small enough, continued treatment of the quenched silicon mass with dimethylamine gas restored reactivity toward the dimethylamine. Scanning electron microscope examination of a mass whose activity had been quenched in this way by monomethylamine showed that the particles were heavily encrusted with a coating that was believed to be polysilazanes. This suggests that these other amines may actually react rapidly with the copper activated silicon, but that the products are not sufficiently volatile to be eluted from the reactor, and instead coat the particles, preventing further reaction.

The copper activated silicon particles and dimethylamine gas can be employed in any suitable amounts commensurate with the size of the reactor used and the amount of dimethylaminosilane product desired. The preferred amounts of reactants will, of course, be those amounts which produce the most optimum results desired and which can be easily determined by routine experimentation. The process of this invention is preferably conducted under autogenous pressure which is generally about 1 atmosphere, however, subatmospheric or superatmospheric pressures may be employed if desired. The rate of reaction will of course, merely depend upon such factors as the reactants, type of reactor, reaction temperature, etc., employed. Suitable reaction temperatures have been given above. The most preferred reaction temperature is about 250° C. since such appears to provide the maximum reaction rate in most instances.

The dimethylaminosilane products of this invention are useful as polymer crosslinking agents, for example in room temperature vulcanizable silicone rubber compositions.

The following examples are illustrative of the present invention and are not to be regarded as limitative. It is to be understood that all parts, percentages and proportions referred to herein and in the appended claims are by weight unless otherwise indicated.

Moreover, in the following examples the particular gas-solid reactor and general processing procedures employed were as follows.

The reactions were conducted in fluidized bed reactors consisting of vertical glass tubes wrapped with heating wires and insulated with asbestos paste, leaving viewing ports for inspecting the bed. A sintered glass disk at the bottom of the tube supported the bed of silicon particles at low gas feed rates. Gases were fed upward through the frit, monitoring feed rates with rotameters and pressure with a mercury U-tube manometer. Two reactors were used: a smaller borosilicate glass tube of 24 mm ID and 62 cm length was suitable for reactions using ca. 100 g silicon, and a larger Vycor ® (Corning Glass Works) reactor of 34 mm ID and 64 cm length was suitable for use with ca 200 g. A thermocouple inserted into the reactor through an axial well extending from the top of the reactor to ca. 5 mm above the frit was used to monitor and control bed temperature. Products left the reactor through a sidearm near the top and were passed into a condensing chamber cooled by a mixture of isopropanol and solid carbon dioxide. The condensed products were collected in a reservoir below this condenser and drawn off through a valve in the bottom of the reservoir. In some experiments a heated cyclone separator was inserted between the reactor tube and the condensing chamber to separate elutriated silicon particles. The condensed products were concentrated by allowing unreacted dimethylamine to distill off at room temperature under an inert atmosphere, then the concentrates were analyzed by gas chromatography on 10% SE-30 columns and the results reported in the Examples below are given as peak area percentages obtained with a thermal conductivity detector. Internal standard experiments confirmed that said percentages approximated the true weight percent composition of the condensate to within about 10 percent.

rates in all fractions demonstrated that the silicon reacted without an induction period.

TABLE I (ANALYSIS OF EXAMPLE 1)

| Fraction | Temp. (°C.) | Duration (hr.) | Me$_2$NH flow [a] | N$_2$ flow [a] | Liquid crude concentrate (g.) | Product analysis [e] % TDS | % lites [f] excluding Me$_2$NH [d] | % heavies [d] | Si consumed %/hr. | Si to TDS. %/hr. |
|---|---|---|---|---|---|---|---|---|---|---|
| A | 252 ± 2 | .67 | 1850 | 250 | 39.8 | 84.6 [c] | .04 | 4.1 | 4.7 | 4.4 |
| B | 247 ± 2 | 1.10 | 1850 | 250 | 60.0 | 90.5 [c] | 2.4 | .9 | 4.7 | 4.6 |
| C | 250 ± 1 | 1.95 | 1850 | 250 | 115.8 | 88.3 [c] | 0.2 | 1.2 | 5.3 | 5.2 |
| D | [b] | [b] | [b] | [b] | .2 | 91.4 [d] | 0.1 | 8.5 | [b] | [b] |

[a] cm$^3$/min at 298° K./804 torr
[b] collected from cyclone after reaction stopped + reactor shut down overnight
[c] internal standard calculation
[d] estimated from relative peak areas
[e] unaccounted-for product is dimethylamine
[f] products eluting before TDS during gas chromatography

EXAMPLE 1

A Vycor reactor as described above was charged with 200 grams of 65×150 mesh copper activated silicon particles prepared by fluidizing a mixture of silicon particles (97.5 parts), cement copper (about 78.5% copper) (2.5 parts) and a small amount (about 0.3 parts) of zinc carbonate with hydrogen chloride gas at about 300° C. until about 5 percent of the silicon had been consumed as chlorosilanes. Dimethylamine and nitrogen gas were introduced to fluidize the copper-silicon particles at 275° C. and the temperature adjusted to 250° C. Fractions of the condensed effluent gases were withdrawn at various intervals and analyzed as shown in Table I below which also contains the processing conditions. Product analysis demonstrates the production of a large amount of tris-dimethylaminosilane (TDS). After standing overnight at room temperature, the reactor was disassembled and 159.1 grams of copper-silicon particles recovered, compared to 164.7 grams expected on the basis of the isolated products and estimated elutriation of said particles. The mass balance for consumed silicon was thus 86 percent. The similarity of

EXAMPLE 2

A Vycor reactor described above was charged with 200 grams of 65×150 mesh copper activated silicon particles prepared as described in Example 1 above. The copper-silicon particle bed was fluidized with nitrogen and heated to 250°-270° C. Dimethylamine gas was then introduced at a room temperature flow rate of 1850 cm$^3$/min. and the nitrogen flow reduced to 250 cm$^3$/min. About 55.4 grams of liquid product (after concentration) was collected over about 1.43 hours and analyzed to give a silicon conversion rate to tris-dimethylaminosilane of 2.7 percent per hour. The copper-silicon particle bed was then fluidized with nitrogen while cooling to room temperature. The bed was then fluidized with a mixture of 250 cm$^3$/min. nitrogen and 1400–2250 cm$^3$/min. of air (dried by passage through a bed of anhydrous calcium sulfate) overnight (about 16 hours). The copper-silicon particle bed was then flushed with nitrogen for 1 hour and heated to 250° C. Fluidization with dimethylamine and nitrogen gas as before produced no isolatable amino containing silane products during 1.68 hours at 250°±3° C. After flushing with nitrogen for 4 hours, the bed was reheated to 324° C. with nitrogen fluidization. The nitrogen feed was reduced to 270 cm$^3$/min. and anhydrous hydrogen chloride gas was fed to the bed at 4000 cm$^3$/min. for 7.5 minutes during which the bed temperature rose to 366° C. and 45.1 grams of chlorosilanes was collected. The reactor was then shut down under nitrogen overnight. Fluidization with dimethylamine and nitrogen gas as before then produced 67.5 grams of condensed liquid product in 1.77 hours at a calculated silicon conversion rate to tris-dimethylaminosilane of 3.0 percent/hour. The mass balance for consumed silicon was 83 percent.

EXAMPLE 3

A Vycor reactor as described above was charged with 200 grams of 65×150 mesh copper activated silicon particles (about 2.9% copper) derived from a copper-silicon alloy prepared by heating 97.25 parts of silicon (32×200 mesh), 2.5 parts of cement copper (a powder mixture of copper and copper oxide, about 78.5% copper) and 0.25 parts of zinc carbonate powder in a rotary calciner to 900°–1000° C. under hydrogen for 45 minutes. Because the copper activated silicon had been stored in air for several months it was treated with anhydrous hydrogen chloride at 300°-375° C. for a total of 12.5 minutes (with a 6 minute interruption midway through this period during which the bed was cooled by nitrogen fluidization), to collect 67.9 grams if chlorosilanes. The copper-silicon particles were then cooled to room temperature after nitrogen fluidization for two hours and stored over the weekend under a slow flow of dry nitrogen. The copper-silicon particles were then heated to 267° C. and dimethylamine gas admitted under the conditions given in Table II below with the flowrate of nitrogen reduced to 260 cm³/min. Fractions of the condensed effluent gases were withdrawn at various intervals and analyzed as shown in said Table II. Product analysis demonstrates the production of a large amount of tris-dimethylaminosilane. Because a temperature controller was not used in this experiment, temperature control was no better than ±3° C. and often considerably worse. About 82.4 grams of blackened copper-silicon was recovered from the reactor. This amount together with an estimated 6.8 grams of elutriated copper-silicon, 16 grams consumed as chlorosilanes and 94.6 grams of silicon contained in the products accounts for about 99 percent of the originally charged copper-silicon particles. The results demonstrate that about 51.4 percent of the reactivated copper-silicon particles was converted into isolatable products with no evidence of loss of mass activity. The silicon conversion rates in Table II indicte a severe loss in tris-dimethylaminosilane (TDS) yield at 200° C. or 300° C., relative to that obtained at 250° C. Heavies (those products boiling at temperatures higher than the boiling point of tris-dimethylaminosilane) also increased appreciably at the higher temperature.

EXAMPLE 4

A borosilicate glass reactor as described above was charged with 100.3 grams of 65×150 mesh silicon particles. Dimethylamine gas was then introduced, replacing the nitrogen, at a flowrate of 1300 cm³/min. (room conditions). Fractions of the condensed product effluent were withdrawn at various intervals and analyzed as shown in Table III below which also contains the processing conditions. Cuprous chloride was added to the silicon bed during the collection of fractions A and B by blowing the finely powdered cuprous chloride with nitrogen through a small port in the side of the reactor tube just above the frit. After fraction D the dimethylamine feed was replaced with nitrogen gas and the silicon bed cooled to room temperature and stored under a positive nitrogen pressure overnight and then reheated to 247° C. before being refluidized with dimethylamine gas.

Product analysis showed the production of a large amount of liquid tris-dimethylaminosilane (TDS) and a small amount of bis-dimethylaminosilane (BDS). The falloff in activity beginning during fraction G is unexplained but may have resulted from air or water contaminants in the feed lines, as minor reactor modifications were made during the experiment. Upon completion of the experiment the recovered silicon bed weighed about 92.7 grams. This example demonstrates the production of dimethylaminosilanes using silicon the cuprous chloride.

TABLE II (ANALYSIS OF EXAMPLE 3)

| Fraction | Temp. (°C.) | Duration (hr) | Me₂NH (cm³/min) | N₂ (cm³/min) | Liq. prod. (g) | Product Analysis [e] | | % lites [f] | Total Si consumed %/hr | Si conv. to TDS %/hr |
|---|---|---|---|---|---|---|---|---|---|---|
| | | | | | | % TDS | % heavies [g] | | | |
| A | 267–243 | 0.75 | 1820 | 260 | 2.9 | 48.8 | ≳22.0 | ~4.8 | 0.3 | 0.2 |
| B [a] | 250 ± 6 | 3.47 | 1820 | 260 | 162.4 | 80.2 | ≳7.3 | ~1.8 | 4.2 | 3.8 |
| C | 234–260° [c] | 2.32 | 1820 | 260 | 122.3 | 85.2 | ≧7.7 | ~2.3 | 5.7 | 5.3 |
| D | 260–305° [b] | 2.00 | 1820 | 260 | 25.0 | 65.6 | ≧15.4 | ~1.1 | 1.3 | 1.1 |
| E [a] | 250 ± 6 | 1.52 | 1820 | 260 | 76.9 | 86.0 | ≧5.1 | ~2.1 | 6.4 | 6.0 |
| F | 245 ± 5 | 1.50 | 1830 | 260 | 70.4 | 74.4 | ≧2.9 | ~1.4 | 5.5 | 5.3 |
| G | 195 ± 2 | 2.32 | 2020 | 260 | 30.5 | 80.6 | ≧1.6 | ~1.2 | 1.7 | 1.7 |
| H [a] | 240–253° [d] | 1.72 | 2020 | 260 | 81.6 | 93.5 | ≧1.8 | ~0.5 | 8.0 | 7.9 |
| Total | | 15.63 | | | 572.0 | | | | | |

[a] overnight shutdown after fraction
[b] 303 ± 2° for 1.67 hr
[c] 250 ± 10° for 2.0 hr
[d] 250 ± 3° for 1.1 hr
[e] most of remainder is Me₂NH
[f] Products boiling at temperatures below the boiling point of tris-dimethylaminosilane (TDS) excluding dimethylamine.
[g] Products with boiling points greater than that of TDS

TABLE III (ANALYSIS OF EXAMPLE 4)

| Fraction | Temp. (°C.) | Duration (hr) | Liq. prod. (g) | Product analysis [d] | | | Si consumed (%/hr) | Si conv. to TDS (%/hr) |
|---|---|---|---|---|---|---|---|---|
| | | | | % TDS | % heavies [e] | % BDS | | |
| A [a] | 251 ± 3 | 0.94 | 0.26 | 59.8 | 13.7 | 0 | 0.05 | 0.04 |
| B [b] | 249 ± 1 | 0.89 | 1.49 | 62.9 | 7.2 | 3.5 | 0.24 | 0.20 |
| C | 247 ± 1 | 1.01 | 7.16 | 69.7 | 3.0 | 11.3 | 1.2 | 0.93 |
| D [c] | 247 ± 1 | 1.02 | 11.59 | 76.3 | 3.2 | 7.3 | 1.9 | 1.6 |
| E | 246 ± 1 | 0.93 | 6.15 | 69.2 | 1.9 | 7.4 | 1.1 | 0.91 |
| F | 246 ± 1 | 0.98 | 11.28 | 64.6 | 1.5 | 6.2 | 1.7 | 1.6 |
| G | 246 ± 2 | 1.04 | 6.26 | 69.6 | 2.9 | 8.3 | 1.0 | 0.85 |
| H | 245 ± 1 | 0.94 | 1.89 | 64.9 | 2.7 | 0.4 | 0.31 | 0.28 |

TABLE III-continued

| | | | (ANALYSIS OF EXAMPLE 4) | | | | |
|---|---|---|---|---|---|---|---|
| | Temp. | Duration | Liq. prod. | Product analysis [d] | | | Si consumed | Si conv. to TDS |
| Fraction | (°C.) | (hr) | (g) | % TDS | % heavies [e] | % BDS | (%/hr) | (%/hr) |
| I | 245 ± 1 | 0.85 | 0 | — | — | — | 0 | 0 |

Notes:
[a] 0.8g Cu₂Cl₂ added 0.13 hr after beginning of this fraction
[b] 1.0g Cu₂Cl₂ added 0.08 hr after beginning of this fraction
[c] Bed was cooled and stored overnight under nitrogen following this fraction
[d] gas chromatographic area percent. Remainder is dimethylamine and non-silicon-containing compounds more volatile than TDS.
[e] products with boiling points greater than that of TDS.

EXAMPLE 5

A Vycor reactor as described above was charged with 200 grams of 65×150 mesh silicon particles and the bed fluidized with nitrogen gas and heated to 308° C. The nitrogen flow was reduced to 250 cm$^3$/min. and anhydrous hydrogen chloride gas introduced at 4000 cm$^3$/min., a rate sufficient to fluidize the bed. The reaction temperature fell and no silicon products were seen produced during a six minute period so the bed temperature was raised to 320° C. while fluidizing with nitrogen again. Anhydrous hydrogen chloride was then reintroduced as before and the temperature began to rise shortly thereafter. During a 22 minute feed of hydrogen chloride at a bed temperature of 315° C. to 360° C., about 106.3 grams of chlorosilanes was collected. The bed was cooled under nitrogen and held under a positive nitrogen pressure over the weekend and then fluidized with nitrogen and reheated to 270° C. Dimethylamine gas was then introduced to fluidized the bed. However, after 3.6 hours of dimethylamine treatment at 205° C. to 298° C., no dimethylaminosilane products were found to be present in the condensed reactor effluent. This example demonstrates that copper is necessary to catalyze and activate the silicon toward reaction with dimethylamine.

EXAMPLE 6

About 100.1 grams of 65×150 mesh copper activated silicon particles (about 2.9% copper) derived from a copper-silicon alloy prepared by heating 97.25 parts of silicon (32×200 mesh), 2.5 parts of cement copper (a powder mixture of copper and copper oxide, about 78.5 copper) and 0.25 parts of zinc carbonate powder in a rotary calciner to 900°-1000° C. under hydrogen for 45 minutes and which did not have any activity toward dimethylamine after having been stored for several months in air was placed in a horizontal Vycor tube and heated to 1000° C. under a slow flow of argon. Hydrogen gas was then substituted for argon for 1 hour at 1000° C. at a gas flowrate of 100 cm$^3$/min. The particle bed was then allowed to cool under argon and 100.1 grams of the copper-silicon particles transferred under nitrogen to a borosilicate glass reactor as described above. The particle bed was then fluidized at 250° C. with nitrogen and then dimethylamine gas introduced at 1300 cm$^3$/min., replacing the nitrogen. Fractions of the condensed effluent gases were withdrawn at various intervals and analyzed as shown in Table IV below which also contains the reaction conditions. Some difficulty in obtaining good fluidization was encountered during Fraction C so the feed rate of dimethylamine was increased as shown. As seen by Table IV below the major product was trisdimethylaminosilane (TDS) along with smaller amounts of bis-dimethylaminosilane (BDS) and tetrakis-dimethylaminosilane (TKDS).

TABLE IV

| | | | | | (ANALYSIS OF EXAMPLE 6) | | | | | | |
|---|---|---|---|---|---|---|---|---|---|---|---|
| | | | Me₂NH | Crude Liquid | Analysis [a] | | | | Total Si | Si conv. | Si conv. |
| | Temp. | Duration | Flowrate | Concentrate | | | | other | consumed | to TDS | to TKDS |
| Fraction | (°C.) | (hr) | [b] | (g) | TDS | BDS | TKDS | heavies [d] | (%/hr) | (%/hr) | (%/hr) |
| A | 250-252 | 4.70 | 1300 | 2.69 | 50.39 | .67 | 27.57 | 5.07 | .07 | .05 | .02 |
| B [c] | 250-252 | 2.21 | 1300 | 35.40 | 69.78 | 6.94 | 1.86 | 1.54 | 2.23 | 1.90 | .04 |
| C | 246-260 | 2.42 | 1300-2000 | 113.56 | 75.87 | 4.10 | 1.12 | 0.79 | 7.43 | 6.79 | .08 |
| D | 248-253 | 0.59 | 2000 | 28.32 | 75.76 | 4.36 | 0.94 | 0.96 | 8.66 | 7.88 | .08 |
| E | 248-253 | 0.79 | 2000 | 39.65 | 72.00 | 4.58 | 0.89 | 1.06 | 9.31 | 8.38 | .08 |
| F | 244-251 | 0.75 | 2000 | 32.59 | 67.66 | 5.52 | 0.87 | 1.13 | 8.35 | 7.35 | .08 |
| G | 248-253 | 0.59 | 2000 | 21.62 | 74.99 | 5.71 | 1.05 | 1.52 | 8.29 | 7.31 | .08 |
| H | 248-253 | 0.74 | 2000 | 27.70 | 67.11 | 5.68 | 0.95 | 0.98 | 8.10 | 7.11 | .09 |
| I | 249-254 | 0.88 | 2000 | 28.23 | 65.43 | 6.08 | 1.65 | 1.36 | 7.38 | 6.37 | .08 |
| J | 248-252 | 0.25 | 2000 | 7.12 | 79.66 | 6.83 | 1.49 | 2.33 | 8.34 | 7.24 | .07 |

[a] glc area percents. Remaining material is Me₂NH and non-Si-containing compounds more volatile than TDS.
[b] cm$^3$/min at 298° K., 797-800 torr
[c] bed cooled and held under N₂ overnight following fraction B
[d] products having boiling points above that of TDS, excluding TKDS

EXAMPLE 7

Copper activated silicon particles were prepared by heating a mixture of 97.5 parts of silicon (65×150 mesh) and 2.5 parts of cement copper (a mixture of copper and copper oxides, about 78.5% copper) to 1000° C. in a horizontal Vycor tube under a slow flow of argon and held at that temperature for 1 hour under hydrogen and finally cooled to room temperature under argon. The copper-silicon particles were stored under nitrogen piror to use.

103.4 Grams of the copper activated silicon particles so prepared was charged to a borosilicate glass reactor as described above and heated to about 250° C. while the bed fluidized with nitrogen. The nitrogen was then replaced with dimethylamine gas at a flowrate of 1300 cm$^3$/min. Fractions of the condensed effluent gases were withdrawn at various intervals and analyzed as shown in Table V below which also contains the processing conditions. For instance, the reactor was shut down three times by replacing the dimethylamine feed with nitrogen and cooling to room temperature, holding the reactor under nitrogen for the desired period, then reheating the particles bed with nitrogen fluidization as before. The times of these shutdowns are noted in said Table V. Gas chromatographic analysis of samples of the reactor effluent during Fractions A and B showed that tetrakis-dimethylaminosilane was being formed at a low rate during these fractions and that trisdimethylaminosilane was absent. However, after condensation to remove a large amount of dimethylamine gas from the product effluent little or no tetrakis-dimethylaminosilane was found in the liquid product Fraction A. Product analysis of the condensed liquid fractions demonstrates the production of a large amount of trisdimethylaminosilane (TDS) along with small amounts of bis-dimethylaminosilane (BDS) and tetrakis-dimethylaminosilane (TKDS). Note that the liquid concentrate of Fraction B was not analyzed, however, silicon conversion rates are provided in Table V based on the composition of the gas samples and estimated residual volatiles.

cles and (2) dimethylamine gas in a gas-solid reactor at a temperature in the range of about 195° C. to about 400° C.

2. A process as defined in claim 1, wherein the reaction is conducted at a temperature of about 230° C. to about 270° C.

3. A process as defined in claim 2, wherein the gas-solid reactor is a fluid bed reactor and whereby the dimethylamine gas is fed to the reactor at a rate sufficient to fluidize the bed of silicon particles.

4. A process as defined in claim 1, wherein at least one dimethylaminosilane is recovered after said reaction.

5. A process as defined in claim 3, wherein the reaction is conducted at a temperature of about 250° C.

6. A process as defined in claim 1, wherein the copper activated silicon is prepared in situ during said process.

7. A process as defined in claim 3, wherein at least one dimethylaminosilane is recovered after said reaction.

8. A process as defined in claim 7, wherein $$H\,Si[N(CH_3)_2]_3$$

TABLE V
(ANALYSIS OF EXAMPLE 7)

| Fraction | Temp. (°C.) | Duration (hr) | Me$_2$NH Flowrate [b] | Crude Liquid Concentrate (g) | Analysis [a] | | | | Total Si heavies consumed [i] (%/hr) | Si conv. to TDS (%/hr) | Si conv. to TKDS (%/hr) |
|---|---|---|---|---|---|---|---|---|---|---|---|
| | | | | | TDS | BDS | TKDS | | | | |
| A [c,h] | 245–251 | 3.31 | 1300 | 0 | — | — | — [h] | — | — | — | — |
| B [f] | 249–251 | 5.57 | 1300 | 0.72 | 0 [g] | 0 [g] | 60 [g] | 0 [g] | .014 [g] | 0 | .014 [g] |
| C [c,d] | 248–252 | 1.57 | 1300 | 3.81 | 51.73 | 8.00 | 6.19 | 8.71 | .32 | .22 | .020 |
| D | 245–253 | 3.58 | 1500 | 16.61 | 58.13 | 9.13 | 1.62 | 5.15 | .64 | .49 | .011 |
| E | 248–252 | 1.86 | 1500 | 47.36 | 66.31 | 5.12 | .63 | 2.27 | 3.69 | 3.23 | .024 |
| F [e] | 248–253 | 1.78 | 1500 | 43.35 | 75.67 | 3.90 | .74 | 2.42 | 4.21 | 3.81 | .029 |
| G [f] | 245–251 | 2.53 | 1500 | 13.71 | 62.92 | 4.54 | 1.48 | 3.50 | .93 | .80 | .015 |
| H | 246–250 | 1.01 | 1500 | 7.76 | 66.40 | 5.70 | 1.25 | 6.57 | 1.49 | 1.23 | .018 |

[a] gas chromatographic area percents. Remaining material is Me$_2$NH and non-Si-containing "lites"
[b] cm$^3$/min at 298° K./800 torr
[c] The reactor was cooled and stored overnight under nitrogen after fractions A and C.
[d] 0.10g CuCl was blown into the bed (along with 0.90g silicon to prevent caking) at the start of fraction C.
[e] The reactor was cooled and stored for five days under nitrogen after fraction F.
[f] Samples of the bed were removed for analysis during fractions B and G.
[g] estimated value based on gas samples. Liquid concentrate was not analyzed.
[h] TKDS was seen in gas samples, but was lost during concentration.
[i] Products less volatile than TDS, excluding TKDS.

Various modifications and variations of this invention will be obvious to a worker skilled in the art and it is to be understood that such modifications and variations are to be included within the purview of this application and the spirit and scope of the appended claims.

What is claimed is:

1. A process for preparing dimethylaminosilane having the formula $$H_{4-a}\,Si[N(CH_3)_2]_a$$

wherein a has a value of 2 to 4 inclusive, said process comprising reacting (1) copper activated silicon partiis produced.

9. A process as defined in claim 7, wherein $$H_2Si[N(CH_3)_2]_2$$

is produced.

10. A process as defined in claim 7, wherein $$Si[N(CH_3)_2]_4$$

is produced.

* * * * *